United States Patent
De Vivo et al.

(10) Patent No.: US 11,008,293 B2
(45) Date of Patent: May 18, 2021

(54) 5-CARBOXAMIDE-2-THIOBARBITURIC ACIDS AND USE THEREOF AS MEDICAMENTS

(71) Applicants: FONDAZIONE ISTITUTO ITALIANO DI TECNOLOGIA, Genoa (IT); UNIVERSITA' DEGLI STUDI DI PADOVA, Padua (IT)

(72) Inventors: Marco De Vivo, Genoa (IT); Jose Antonio Ortego Martinez, Genoa (IT); Claudia Sissi, Cadoneghe (IT); Jose Manuel Arencibia Jimenez, Genoa (IT)

(73) Assignees: UNIVERSITÀ DEGLI STUDI DI PADOVA, Padua (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 16/494,433

(22) PCT Filed: Mar. 15, 2018

(86) PCT No.: PCT/EP2018/056469
§ 371 (c)(1),
(2) Date: Sep. 16, 2019

(87) PCT Pub. No.: WO2018/167187
PCT Pub. Date: Sep. 20, 2018

(65) Prior Publication Data
US 2020/0087263 A1  Mar. 19, 2020

(30) Foreign Application Priority Data
Mar. 15, 2017 (IT) .................. 102017000028709

(51) Int. Cl.
C07D 239/66 (2006.01)
A61K 45/06 (2006.01)

(52) U.S. Cl.
CPC ............ C07D 239/66 (2013.01); A61K 45/06 (2013.01)

(58) Field of Classification Search
CPC ............................. C07D 239/66; A61K 45/06
USPC ......................................................... 514/271
See application file for complete search history.

(56) References Cited

U.S. PATENT DOCUMENTS 4,879,276 A    11/1989  Brewer

FOREIGN PATENT DOCUMENTS

GB    2152047 A    7/1985
JP    S60166669 A   8/1985

OTHER PUBLICATIONS

International Search Report and Written Opinion for corresponding Application No. PCT/EP2018/056469 (dated Jun. 19, 2018).

*Primary Examiner* — Kahsay Habte
(74) *Attorney, Agent, or Firm* — Troutman Pepper Hamilton Sanders LLP (Rochester)

(57) ABSTRACT

The invention relates to a class of 5-carboxamide-2-thiobarbituric acid derivatives which inhibits human type II topoisomerase (topoII) enzyme and to use thereof as medicaments especially for blocking the proliferation of cancer cells and treating cancer. The invention also provides a method for the manufacture of the 5-carboxamide-2-thiobarbituric acid derivatives.

20 Claims, No Drawings

5-CARBOXAMIDE-2-THIOBARBITURIC ACIDS AND USE THEREOF AS MEDICAMENTS

This application is a national stage application under 35 U.S.C. § 371 of PCT Application No. PCT/EP2018/056469, filed Mar. 15, 2018, which claims the priority benefit of Italy Patent Application No. 102017000028709, filed Mar. 15, 2017.

FIELD OF THE INVENTION.

The present invention concerns with 5-carboxamide-2-thiobarbituric acids as type II topoisomerase inhibitors and use thereof as medicaments.

The present invention origins in the pharmaceutical field and especially in the field of chemical compounds for the treatment of cancer.

Specifically, the present invention related to a family of 5-carboxamide derivatives of 2-thiobarbituric acids that inhibit human type II topoisomerase (topoII) enzyme and that are useful as anticancer agents.

Background of the Invention

Topoisomerases are enzymes that modulate the topological state of DNA in the cell. The scientific article "DNA topoisomerase II and its growing repertoire of biological functions", Nitiss J L. *Nature Reviews Cancer* (2009), 9(5), 327-337 reports that the activity of these enzymes is performed by introducing transient breaks in the DNA strand, thus catalyzing DNA unwinding, an essential step in, for example, transcription and replication.

As reported in the publication "The DNA cleavage reaction of topoisomerase II: wolf in sheep's clothing" Deweese J E et al. *Nucleic Acids Research* (2009), 37(3), 738-748, topoisomerases are classified in two major classes, type I and II, based on the number DNA strands that they cleave and on their mechanism of action. Type II topoisomerases, also known as topo II, are essential for cell survival and play vital roles in virtually every nucleic acid process, including DNA replication, transcription, and recombination.

They also are required for proper chromosome organization and segregation as discussed in the article "Topoisomerase II and leukemia", Pendleton M. et al. *Annals of the New York Academy of Sciences* (2014), 1310(1), 98-110 Human topo II enzymes are essential for DNA topology modification, and represent a validated drug target to treat cancer.

Several classes of drugs that target topo II have been developed over the last few decades and used in the clinics for the treatment of different types of cancer.

For example, epipodopodophyllotoxin compounds, like etoposide, are used to treat lung cancer, choriocarcinoma, ovarian and testicular cancers, lymphoma, and acute myeloid leukemia. Other members of topoisomerase inhibitors belonging to this group, like the drug teniposide, are approved by the Health Authorities for the treatment of central nervous system tumors, malignant lymphoma, and bladder cancer.

Another wide class of topoisomerase inhibitors is represented by anthracyclines, which are used for the treatment of many different types of solid tumors and hematologic cancers. Moreover the scientific publication "Contemporary challenges in the design of topoisomerase II inhibitors for cancer chemotherapy" Bailly C. *Chemical Review* (2012), 112(7), 3611-3640 discloses the use of anthraquinones in the treatment of advanced prostate cancer and in certain forms of leukemia.

The same authors of the present application in the not yet published Italian patent application No. IT102016000130706 have disclosed substituted biciclyc pyrimidines compounds as type II topoisomerase inhibitors and their use as medicaments.

Although a lot of efforts have been made in the development of new drugs targeting type II topoisomerase, major shortcomings of these drugs are represented by their elevated toxicity in addition to the appearance of drug-resistance (Non-quinolone Inhibitors of Bacterial Type IIA Topoisomerases: A Feat of Bioisosterism. Mayer C. et al. *Chemical Reviews* (2014), 114 (4), 2313-2342).

Thus, at present there still be an unmet medical need for novel topo II inhibitors for the treatment of cancer with are safe and are provided with anticancer activity. One of the objects of the present invention is therefore to provide compounds acting as inhibitors of human type II topoisomerase (topo II) enzymes which are effective in the treatment of cancer and possibly well tolerated by the human body.

SUMMARY OF THE INVENTION

The inventors have found that a class of compounds having a 5-carbamoyl-2-thiobarbituric scaffold having certain substituents in selected positions of the phenyl group, are effective inhibitors towards human type II topoisomerase (topo II) enzymes and are active in blocking the proliferation of cancer cells.

Accordingly, in one aspect the present invention provides a compound having the formula (I) or enantiomers and/or pharmaceutically salts thereof, as defined in claim 1

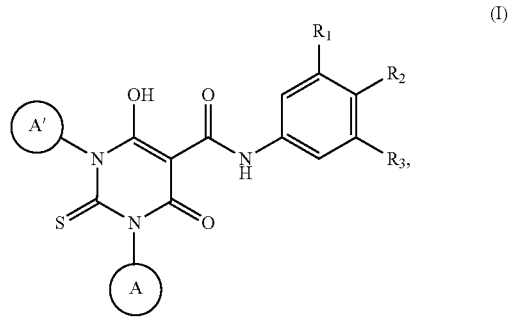

for use as a medicament.

In accordance with a second aspect, the present invention provides a compound having the formula (I) as defined in claim 1 or enantiomers or pharmaceutically acceptable salts thereof

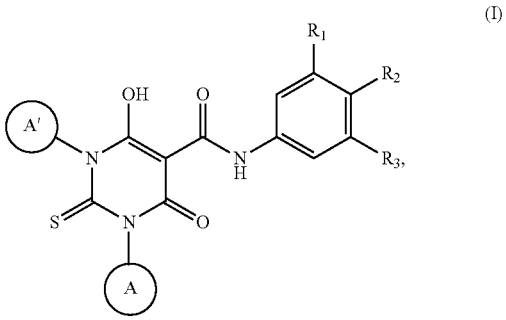

(I)

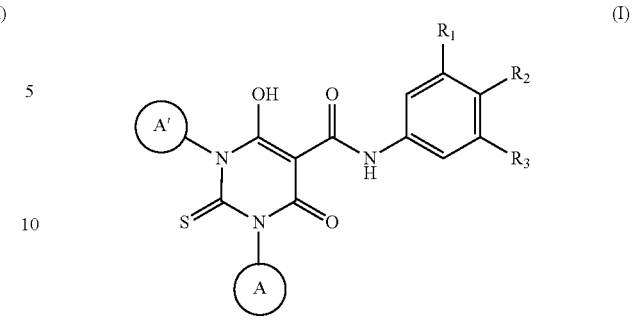

(I)

for use in the treatment of cancer.

In accordance with a third aspect, the present invention provides a method for the treatment of cancer in a subject comprising the administration of an effective amount of a compound of the above referred formula (I), or a pharmaceutically acceptable salt thereof.

The present invention also describes methods the preparation of the compounds of the above formula (I) or pharmaceutically acceptable salts thereof.

In a yet further aspect, the present invention relates to pharmaceutical compositions comprising a compound of formula (I) or pharmaceutically acceptable salts thereof as defined in claim 1, and a pharmaceutically acceptable carrier and/or excipient.

DETAILED DESCRIPTION OF THE INVENTION

The present invention origins from the finding that compounds having 5-N aryl-carboxamide-2-thiobarbituric scaffold bearing certain substituents in selected positions of the phenyl ring linked to the carboxamide group show a high and specific inhibitory activity against human type II topoisomerase (topo II) enzyme making these compounds effective in the treatment of cancer.

The inventors also found that compounds having 5-N-aryl-carboxamide-2-thiobarbituric scaffold bearing selected substituents in the para positions of the phenyl ring linked to the carboxamide group have an increased anticancer activity compared to unsubstituted compounds.

The inventors also found that compounds of formula (I) as defined before are potent inhibitors towards human type II topoisomerase enzymes, showing $IC_{50}$ values in the 5-200 micromolar range, which match that of current topo II-targeted clinical drugs.

One of the peculiarities of the here disclosed compounds of formula (I) is the increased ability of a subset of compounds to stabilize the cleavage complex.

In the following Table 1, the poison mechanism inhibition for some compounds is confirmed while cleavage complex stabilization is observed. This activity is shared with important drugs currently used in the clinic.

I. Medical Use of Compounds of Formula (I)

According to an aspect of the invention, compounds of formula (I) or pharmaceutically acceptable salts thereof, are provided for use in the treatment of cancer are provided, wherein R1, R2, R3 are independently hydrogen, halogen, hydroxyl, alkoxyalkyl containing a total of 1 to 4 carbon atoms, amino, aminoalkyl containing a total of 1 to 4 carbon atoms, aminodialkyl containing a total of 2 to 8 carbon atoms, and wherein at least one of $R_1$, $R_2$, $R_3$ is not H;

Ⓐ and are independently an optionally substituted heteroaromatic 6-membered ring containing 1 or 2 nitrogen atoms or an optionally substituted 6-membered aryl.

The compounds of formula (I) as defined above, are shown to be selective and effective type II topoisomerase (topoII) enzyme activity inhibitors.

In accordance with certain embodiments, at least one of the rings Ⓐ and is an optionally substituted aryl, more preferably an optionally substituted phenyl.

According to preferred embodiments, both the moieties Ⓐ and are aryl, especially phenyl which optionally may be substituted as described herein above.

In accordance with anyone the above embodiments, the aryl optionally may be substituted with a group $C_1$-$C_6$ alkyl, $C_1$-$C_6$ alkoxyl, hydroxyl, amino, aminoalkyl containing a total of 1 to 4 carbon atoms, aminodialkyl containing a total of 2 to 8 carbon atoms.

In accordance with certain embodiments each of the moieties Ⓐ and are an optionally substituted heteroaromatic 6-membered ring containing 1 nitrogen atoms such as pyridine.

In accordance with certain embodiments each of the moieties Ⓐ and are an optionally substituted heteroaromatic 6-membered ring containing 2 nitrogen atoms such as pyridazine, pyrimidine, pyrazine or diazines.

In certain embodiments the substituents $R_1$, $R_2$, $R_3$ are each independently hydrogen with the proviso that at least one substituent of is not H, hydroxyl, alkoxyalkyl containing of 1 to 4 carbon atoms and at least one of the moieties Ⓐ and are an optionally substituted aryl, preferably a phenyl which optionally may be substituted with a group $C_1$-$C_6$ alkyl, alkoxyl or hydroxyl.

Further embodiments of compounds of formula (I) are defined in the appended dependent claims 6-9.

In accordance to a preferred embodiment, the both rings Ⓐ and are phenyl and the substituent groups $R_1$, $R_2$, $R_3$ are selected from the group consisting of, hydroxyl and methoxyl.

According to a preferred embodiment, the rings Ⓐ and are a phenyl ring, $R_1$ and $R_2$ are hydrogen and $R_3$ is methoxyl.

II. Methods of Treatment

The present invention also provides compounds of Formula (I) or pharmaceutically acceptable salts thereof, for inhibiting the activity of type II topoisomerase (topo II) enzymes.

According to certain aspects of the present invention, compounds of Formula (I), their salts, and pharmaceutical compositions containing them, as defined hereinabove are useful in treating diseases or disorders involving increased, type II topoisomerase (topo II) enzymatic activity, compared to physiological.

The treatment with the compounds of the invention may be prophylactic or therapeutic.

The subject to be treated may be an animal (e.g., mouse, rat, non-human primate and non-human mammal) or human.

In accordance with a third aspect, the present invention provides a method for the treatment of cancer in a subject comprising the administration of an effective amount of a compound of the above referred formula (I), according to anyone of the embodiments described herein above or a pharmaceutically acceptable salt or enantiomer thereof.

The compounds of Formula (I) may or may not be administered simultaneously, separately or sequentially with another anticancer agent.

The diseases and disorders which may be treated with the compounds of the invention include, but are not limited to, primary and metastatic neoplastic diseases or, in general, involving cell overproliferation, inflammatory related conditions or pain.

Diseases and disorders involving cell overproliferation include, but are not limited to, pre-malignant conditions, for example hyperplasia, metaplasia or dysplasia, cancers, cancer metastasis, benign tumors, hyperproliferative disorders and benign dysproliferative disorders.

Primary and metastatic neoplastic diseases and related disorders that can be treated and/or prevented by the methods, compounds and compositions of the presently disclosed subject matter include, but are not limited to prostate and lung cancer, colorectal cancer, liver cancer, prostate cancer, head and neck cancer, breast cancer, choriocarcinoma, ovarian and testicular cancers, lymphoma, and acute myeloid leukemia, central nervous system tumors, malignant lymphoma and bladder cancer, metastatic melanoma, precancerous skin conditions such as actinic keratosis, skin cancers such as squamous cell carcinoma and basal cell carcinoma, and hematological malignancies such as chronic myelogeneous leukemia.

In some embodiments, the compounds of Formula (I) and their pharmaceutical compositions and methods of administering them, are useful in treating or preventing a disease or disorder when administered in combination with other treatments.

In an additional aspect, the present invention also concerns combination therapies or treatment with a compound of formula (I), or pharmaceutical composition containing them.

In some embodiments, the compounds of Formula (I) and their pharmaceutical compositions and methods of administering them, are useful in treating various cancers when administered in combination with other pharmacological agents or active ingredients.

In certain embodiments, these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafururacil (UFT), dacarbazine, fenretinide, camptothecin, irinotecan, fludarabine, vinblastine, taxol, mitomycin C.

In some embodiments, the compounds of Formula (I), and their pharmaceutical compositions and methods of administering them, are useful in treating various cancers when administered before, during or after patient's treatment with radiation therapy.

III. Pharmaceutically Acceptable Salts

It will be understood that, as used herein, references to the compounds of Formula (I), are meant to include also the pharmaceutically acceptable salts or derivatives thereof.

Furthermore, the compound of the formula (I), may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I)" refer to each of the compounds of Formulae (I), are meant to include also their hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the hydrochloride, acetate, hydrobromide, sulfate, phosphate, methane or ethane sulfonate, acetate, citrate, gluconate, lactate, tartrate, phosphate, borate, maleate, oxalate, succinate, fumarate benzoate, salicylate, phenylacetate, or mandelate, sulphate and nitrate, the hydrochloride being preferred.

Alternatively, the salt may be a salt of a metal which typically is selected from the IA or IIA groups of the periodic table of elements.

The salts of compounds of Formula (I) may be prepared by reacting a basic compound with the desired acid in solution.

Physiologically or pharmaceutically acceptable salts are particularly suitable for medical applications because of their greater aqueous solubility relative to the parent compounds.

Pharmaceutical acceptable salts may also be prepared from other salts, including other pharmaceutically acceptable salts, of the compounds of Formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of Formula I may readily be isolated in association with solvent molecules by crystallisation or evaporation of an appropriate solvent to give the corresponding solvates.

IV. Pharmaceutical Compositions

In a fourth aspect, the invention provides pharmaceutical compositions of compounds of Formula (I). The pharmaceutical compositions of the present invention encompass any compositions made by admixing a compound of the present invention and a pharmaceutically acceptable carrier. Such compositions are suitable for pharmaceutical use in an animal or human. The pharmaceutical compositions of the present invention comprise a therapeutically effective amount of one or more compounds of Formula (I), or a pharmaceutically acceptable salt thereof, and a pharmaceutically acceptable carrier. A pharmaceutical composition may optionally contain other active ingredients.

The term "carrier" refers to a vehicle, excipient, diluent, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral including subcutaneous, intramuscular and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous or pulmonary, in the form of nasal or buccal inhalation, administration. The compositions may be prepared by any of the methods well-known in the art of pharmacy. The pharmaceutical compositions may be in the form of tablets, pills, capsules, solutions, suspensions, emulsion, powders, suppository and as sustained release formulations. If desired, tablets may be coated by standard aqueous or non-aqueous techniques. In certain embodiments such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the gastrointestinal tract, the composition may be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I), or a salt thereof, and the powder of a suitable carrier and/or lubricant. The compositions for pulmonary administration can be inhaled from any suitable dry powder inhaler device known to a person skilled in the art. Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I), per dosage unit for daily administration. In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation. When used in combination with one or more other active ingredients, the compound of the present invention and the other active ingredients may be used in lower doses than when each is used singly. With respect to formulations with respect to any variety of routes of administration, methods and formulations for the administration of drugs are disclosed in *Remington's Pharmaceutical Sciences, 17th Edition*, Gennaro et al. Eds., Mack Publishing Co., 1985, and *Remington's Pharmaceutical Sciences*, Gennaro A R ed. 20th edition, 2000, Williams & Wilkins PA, USA, and *Remington: The Science and Practice of Pharmacy, 21st Edition*, Lippincott Williams & Wilkins Eds., 2005; and in *Ansel's Pharmaceutical Dosage Forms and Drug Delivery Systems, 8th Edition*. Lippincott Williams & Wilkins Eds., 2005, which are herein incorporated as reference.

V. Definitions

All technical and scientific terms used herein have the same meaning as commonly understood by a person of ordinary skill in the art, unless otherwise defined. The following terms, used in the specification and claims of this application, have the meaning specified hereunder, unless otherwise defined.

The term "alkyl", as used herein, indicates a saturated aliphatic hydrocarbon radical, including straight chain and branched chain radicals of 1 to 6 carbon atoms referred to as $C_{1-6}$ alkyl. Non-limiting examples of alkyl are methyl, ethyl, propyl, isopropyl, n-butyl, iso-butyl, tert-butyl, n-amyl, isoamyl, n-hexyl, and the like.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like. The term MeO means methoxy, the term EtO means ethoxy.

The term "aryl" means an aromatic ring wherein each of the atoms forming the ring is a carbon atom. Aryl rings may be formed by five to nine carbon atoms. Typically in the present invention are six-membered aryl, that is formed of six atoms. Examples of aryl groups include but are not limited to phenyl, naphthalenyl.

The term heteroaromatic ring (heteroaryl) refers to an aryl group that includes one or more ring heteroatoms especially nitrogen. The term "heteroaromatic 6-membered ring containing 1 or 2 nitrogen atoms" means a six-membered aromatic ring in which one or two of the atoms of the ring, respectively, are a nitrogen atom.

The term "hydroxy" means a —OH radical.

The term aminoalkyl means an amino group functionalized with one alkyl group, such as —NH($C_1$-$C_6$)alkyl.

The term diaminoalkyl means an amino group functionalized with two ($C_1$-$C_{10}$) alkyl groups.

The term "trifluoromethoxy" means a —$OCF_3$ radical.

The term "alkylalkoxy" means an alkyl group functionalized with one or more alkoxy group, like $CH_2$—O—$CH_3$.

The term "halogen" means fluoro, chloro, bromo or iodo. A preferred halogen is fluoro.

In the present application the terms rings A and A' means rings or moieties Ⓐ and , respectively.

VI. Process for Preparing Compounds of Formula (I)

Compounds of Formula (I), provided herein that inhibit the activity of topo II, may be synthesized using synthetic techniques described herein. The reactions can be employed in a linear sequence to provide the compounds described herein or they may be used to synthesize fragments which are subsequently joined by the methods described herein and/or known in the art.

According to a further aspect, a method for the manufacture of compounds of formula (I) is provided according to the following reaction Schemes 1, 2.

Scheme 1

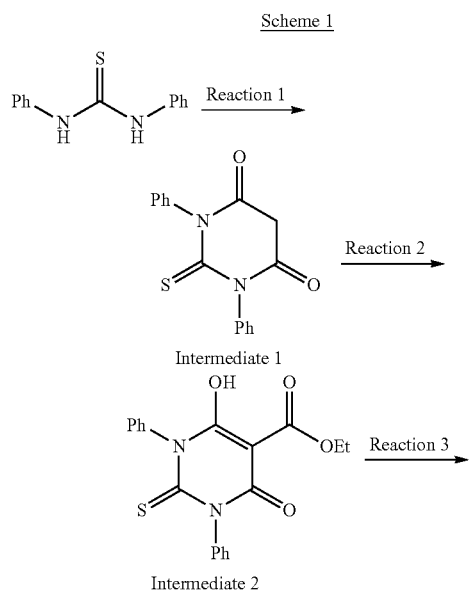

Intermediate 1

Intermediate 2

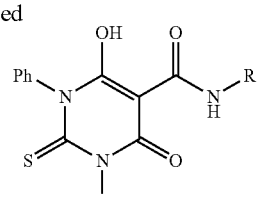

Reaction 1. Step 1. Methyl 3-chloro-3-oxopropionate (2.2 eq), DCM (dry), $N_2$, rt, 16 h, rt. Step 2. Low pressure, rt, 72 h, yield 85%
Reaction 2. Ethylchloroformate (1.05 eq), DMAP (0.08 eq), pyridine (1.25 eq), DCM, $N_2$, 0° C. to rt, 16 h, yield 71%.
Reaction 3. R—$NH_2$ (1eq), DMF, $N_2$, 100° C., 30 min.

R =

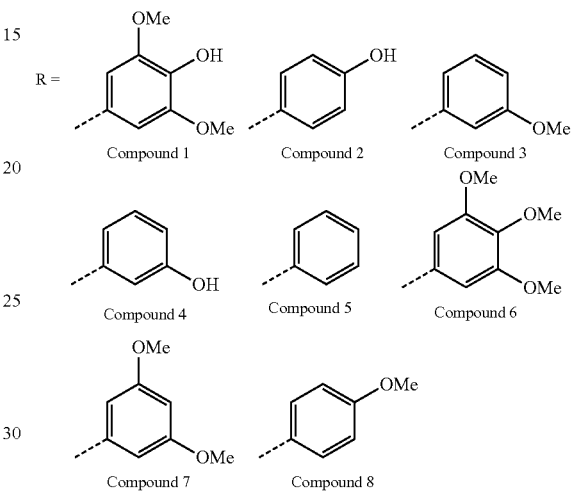

Scheme 2

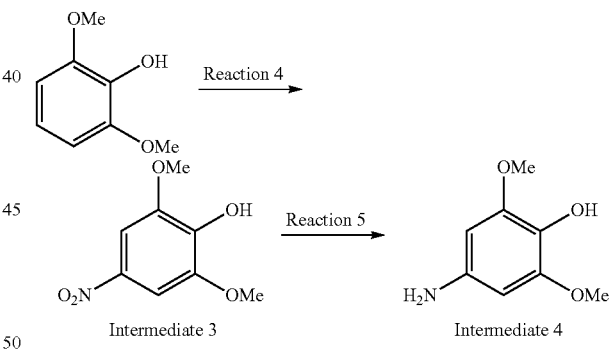

Reaction 4. tert-butyl nitrite (3 eq), THF (dry), rt, 30 min, yield 24%.
Reaction 5. 1,4-cyclohexadiene (20 eq), Pd—C, EtOH, $N_2$, rt, 16 h, yield 99%.

Specifically, in accordance with the reaction scheme 1, the process of the invention comprises the steps of
a) Adding methyl 3-chloro-3-oxopropionate to a solution of N,N'-Diphenylthiourea in an organic solvent, preferably dichloromethane to give 1,3-Diphenyl-2-thiobarbituric acid (Intermediate 1),
b) Adding ethyl chloroformate to a solution of the Intermediate 1 in 4-dimethylamino-pyridine and pyridine in an organic solvent, preferably dichloromethane to give ethyl 4-hydroxy-6-oxo-1,3-diphenyl-2-thioxo-pyrimidine-5-carboxylate (Intermediate 2)
c) Reacting Intermediate 2 with aniline R—$NH_2$ in presence of an organic solvent, preferably dymethylformamide, preferably under $N_2$ atmosphere, wherein R represents

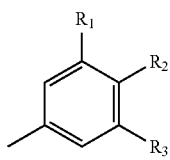

wherein $R_1$, $R_2$, $R_3$ are independently hydrogen provided that at least one of $R_1$, $R_2$, $R_3$ is not H, halogen, hydroxyl, alkoxyalkyl containing a total of 1 to 4 carbon atoms, amino, aminoalkyl containing a total of 1 to 4 carbon atoms, aminodialkyl containing a total of 2 to 8 carbon atoms, to give the compound of formula (I).

In accordance with the reaction scheme 2, the process of the invention comprises the steps of
a) Adding tert-Butyl nitrite to a solution of 2,6-dimethoxyphenol in an organic solvent preferably tetrahydrofuran, to give 2,6-dimethoxy-4-nitro-phenol (Intermediate 3)
b) Adding 1,4-cyclohexadiene to Intermediate 3 in presence of a catalyzer, preferably Palladium on activated carbon suspension in ethanol to give 4-amino-2,6-dimethoxy-phenol (Intermediate 4).

With the aim of better illustrating the present invention, without limiting it, exemplary compounds of the invention with their activity data are reported in the Table 1 of Example 10.

Working examples of the present invention are hereinafter provided for illustrative and non-limiting purposes, together with examples of evaluating the inhibitory capacity of the described compounds.

EXAMPLES

General Considerations on Chemical Experiments

All the commercial available reagents and solvents were used as purchased from vendors without further purification. Dry solvents were purchased from Sigma-Aldrich. Automated column chromatography purifications were done using a Teledyne ISCO apparatus (CombiFlash® Rf) with pre-packed silica gel columns of different sizes (from 4 g up to 120 g) and mixtures of increasing polarity of cyclohexane and ethyl acetate (EtOAc), cyclohexane and tert-ButylMethyl eter (TBME) or dicloromethane (DCM) and methanol (MeOH). NMR experiments were run on a Bruker Avance III 400 system (400.13 MHz for 1H, and 100.62 MHz for 13C), equipped with a BBI probe and Z-gradients. Spectra were acquired at 300 K, using deuterated dimethylsulfoxide (DMSO-$d_6$) or deuterated chloroform (CDCl$_3$) as solvents. For 1H-NMR, data are reported as follows: chemical shift, multiplicity (s=singlet, d=doublet, dd=double of doublets, t=triplet, q=quartet, m=multiplet), coupling constants (Hz) and integration. UPLC/MS analyses were run on a Waters ACQUITY UPLC/MS system consisting of a SQD (single quadrupole detector) mass spectrometer equipped with an electrospray ionization interface and a photodiode array detector. The PDA range was 210-400 nm. Analyses were performed on an ACQUITY UPLC BEH C18 column (100× 2.1 mmID, particle size 1.7 μm) with a VanGuard BEH C18 pre-column (5×2.1 mmID, particle size 1.7 μm). Mobile phase was 10 mM NH$_4$OAc in H$_2$O at pH 5 adjusted with CH$_3$COOH (A) and 10 mM NH$_4$OAc in CH$_3$CN—H2O (95:5) at pH 5.0. Two types of gradients were applied depending on the analysis, gradient 1 (5% to 100% mobile phase B in 3 min) or gradient 2 (50% to 100% mobile phase B in 3 min). Electrospray ionization in positive and negative mode was applied. Electrospray ionization in positive and negative mode was applied. ESI was applied in positive and negative mode. All tested compounds showed ≥90% purity by NMR and UPLC/MS analysis.

Example 1

Synthesis

General procedure, reaction 3 (between Intermediate 2 and appropriate aniline) according to Scheme 1. Amide formation.

A mixture of corresponding N,N-diphenyl-5-ethylcarboxylate-2-thiobarbituric acid intermediate 2 (1 mmol) and an appropriate aniline (1 mmol) in dry DMF (1 ml) was stirred at 100° C. for 30 minutes, then cooled to room temperature, poured into water (10 ml), the resulting solid filtrated, rinsed twice with water (2×10 ml) and methanol (2×5 ml) finally yielding titled compound.

Example 2

Synthesis of 4-hydroxy-N-(4-hydroxy-3,5-dimethoxy-phenyl)-6-oxo-1,3-diphenyl-2-thioxo-pyrimidine-5-carboxamide Step 1. Synthesis of 1,3-Diphenyl-2-thiobarbituric Acid (Intermediate 1, Scheme 1)

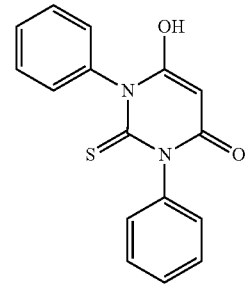 [SMILES: O=c1cc(O)n(-c2ccccc2)c(=S)n1-c1ccccc1]

Under N$_2$ atmosphere, Methyl 3-chloro-3-oxopropionate (2.1 ml, 18.9 mmol) was dropwise added to a solution of N,N'-Diphenylthiourea (2.0 g, 8.6 mmol) in dry DCM (100 ml) and the reaction crude stirred at room temperature for 16 hours. Afterwards, the reaction crude was concentrated to dryness at low pressure and the resulting oil stored under vacuum at room temperature until converted into a solid, total time 72 hours. Finally, resulting solid was solved in the minimum DCM volume (10 ml) and slowly poured onto cold cyclohexane (100 ml). Resulting yellowish solid filtration yielded 2.16 g of title compound (yield 85%).

Characterization: Rt=1.32 min; MS (ESI) m/z: 295.1 [M-H]$^-$, [M-H]$^-$ calculated: 295.1. 1H-NMR (400 MHz, CDCl$_3$) δ 7.57-7.39 (m, 6H), 7.25-7.18 (m, 4H), 4.11 (s, 2H).

Step 2. Synthesis of ethyl 4-hydroxy-6-oxo-1,3-diphenyl-2-thioxo-pyrimidine-5-carboxylate (Intermediate 2, Scheme 1)

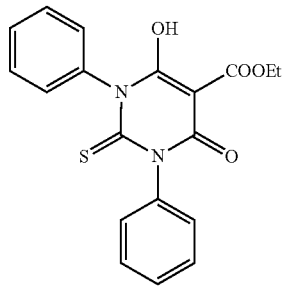 [SMILES: CCOC(=O)c1c(O)n(-c2ccccc2)c(=S)n(-c2ccccc2)c1=O]

Under $N_2$ atmosphere, Ethyl chloroformate (630.4 mg, 5.81 mmol) was dropwise added to a 0° C. solution of Intermediate 1 (1.64 g, 5.53 mmol), 4-dimethylamino-pyridine (54 mg, 0.44 mmol) and pyridine (546.8 mg, 6.91 mmol) in dry DCM (4.1 ml). The reaction crude was allowed warming to room temperature, stirred for 16 hours, diluted with DCM (21 ml), washed with water (25 ml), dried over $Na_2SO_4$ and concentrated to dryness at low pressure. Trituration in DCM (5 ml) yielded titled compound obtaining 1.45 g of pure compound (71% yield).

Characterization: Rt=1.42 min; MS (ESI) m/z: 369.1 [M-H]$^+$, [M-H]$^+$ calculated: 369.1 1H-NMR (400 MHz, DMSO-$d_6$) δ 7.35 (t, J=7.6 Hz, 4H), 7.25 (t, J=7.3 Hz, 2H), 7.10 (d, J=7.7 Hz, 4H), 4.00 (q, J=7.1 Hz, 2H), 1.14 (t, J=7.1 Hz, 3H).

Step 3. Synthesis of 2,6-dimethoxy-4-nitro-phenol (Intermediate 3, Scheme 2)

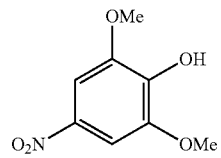 [SMILES: COc1cc([N+](=O)[O-])cc(OC)c1O]

tert-Butyl nitrite (12.6 ml, 95.36 mmol) was added to a solution of 2,6-dimethoxyphenol (5 g, 31.79 mmol) in THF (160 ml), then was stirred for 30 minutes at room temperature and concentrated to dryness at low pressure. Purification by typical silica gel flash chromatography (cyclohexane/EtOAc from 90:10 to 70:30) afforded the pure title compound (1.5 g, yield 24%).

Characterization: Rt=1.70 min, m/z 198.1, [M-H]$^-$, [M-H]$^-$ calculated: 198.0. 1H-NMR (400 MHz, CDCl$_3$) δ 7.57 (s, 2H), 6.08 (s, 1H), 3.98 (s, 6H).

Step 4. Synthesis of 4-amino-2,6-dimethoxy-phenol (Intermediate 4, Scheme 2)

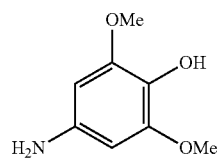

Under $N_2$ atmosphere, 1,4-cyclohexadiene (1 ml, 10.04 mmol) was added to a 4-nitro-2,6-dimethoxy-phenol (100 mg, 0.50 mmol) and Palladium on activated carbon (100 mg) suspension in ethanol (10 ml) and stirred at room temperature for 16 hours, then the catalyst was filtered off through a celite coarse patch, the filtrate concentrated to dryness at low pressure yielding titled compound pure enough to be used in the next step (85 mg, yield 99%).

Characterization: Rt=0.68 min; MS (ESI) m/z: 168.1 [M-H]$^-$, [M-H]$^-$ calculated: 168.0. 1H-NMR (400 MHz, DMSO-$d_6$) δ 7.15 (s, 1H), 5.88 (s, 2H), 4.52 (s, 2H), 3.65 (s, 6H).

Step 5. Synthesis of 4-hydroxy-N-(4-hydroxy-3,5-dimethoxy-phenyl)-6-oxo-1,3-diphenyl-2-thioxo-pyrimidine-5-carboxamide (Compound 1, Scheme 1)

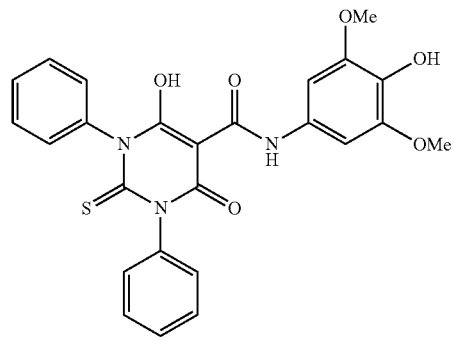 [SMILES: COc1cc(NC(=O)c2c(O)n(-c3ccccc3)c(=S)n(-c3ccccc3)c2=O)cc(OC)c1O]

Titled compound was synthesized following the general procedure previously described using intermediate 2 (200 mg, 0.51 mmol) and 4-amino-2,6-dimethoxy-phenol (63.8 mg, 0.51 mmol) obtaining 15.7 mg of pure compound (yield 16%).

Characterization: Rt=1.96 min; MS (ESI) m/z: 492.1 [M-H]$^+$, [M-H]$^+$ calculated: 492.1. 1 H-NMR (400 MHz, CDCl$_3$): 11.82 (s, 1H), 7.58-7.47 (m, 6H), 7.31 (dd, J=7.4, 3.1 Hz, 4H), 6.76 (s, 2H), 5.47 (s, 1H), 3.86 (s, 6H).

Example 3

Synthesis of 4-hydroxy-N-(4-hydroxyphenyl)-6-oxo-1,3-diphenyl-2-thioxo-pyrimidine-5-carboxamide (Compound 2, Scheme 1)

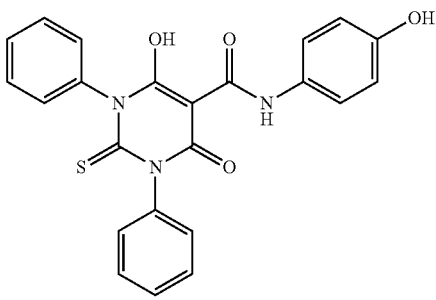 [SMILES: O=C(Nc1ccc(O)cc1)c1c(O)n(-c2ccccc2)c(=S)n(-c2ccccc2)c1=O]

Titled compound was synthesized following the general procedure previously described using intermediate 2 (100 mg, 0.27 mmol) and 4-aminophenol (30.0 mg, 0.27 mmol) obtaining 25.1 mg of pure compound (yield 22%). Rt=2.10 min; MS (ESI) m/z: 432.1 [M-H]⁻, [M-H]⁻ calculated: 432.1. 1H-NMR (400 MHz, DMSO-d₆) δ 11.49 (s, 1H), 9.64 (s, 1H), 7.48 (t, J=7.5 Hz, 4H), 7.40 (t, J=7.3 Hz, 2H), 7.34-7.32 (m, J=8.2, 3.2 Hz, 6H), 6.78 (d, J=8.8 Hz, 2H).

Example 4

Synthesis of 4-hydroxy-N-(3-methoxyphenyl)-6-oxo-1,3-diphenyl-2-thioxo-pyrimidine-5-carboxamide (Compound 3, Scheme 1)

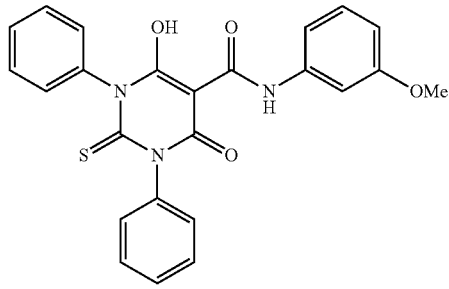 [SMILES: COc1cccc(NC(=O)c2c(O)n(-c3ccccc3)c(=S)n(-c3ccccc3)c2=O)c1]

Titled compound was synthesized following the general procedure previously described using intermediate 2 (100 mg, 0.27 mmol) and m-anisidine (0.031 ml, 0.27 mmol) obtaining 66.1 mg of pure compound (yield 55%).

Characterization: Rt=2.10 min; MS (ESI) m/z: 446.1 [M-H]⁺, [M-H]⁺ calculated: 446.1. 1H-NMR (400 MHz, CDCl₃) δ 11.85 (s, 1H), 7.62-7.52 (m, 4H), 7.52-7.45 (m, 2H), 7.40-7.28 (m, 4H), 7.27 (d, J=4.4 Hz, 2H), 7.13-7.01 (m, 2H), 6.78 (dd, J=8.2, 2.4 Hz, 1H), 3.79 (s, 3H).

Example 5

Synthesis of 4-hydroxy-N-(3-hydroxyphenyl)-6-oxo-1,3-diphenyl-2-thioxo-pyrimidine-5-carboxamide (Compound 4, Scheme 1)

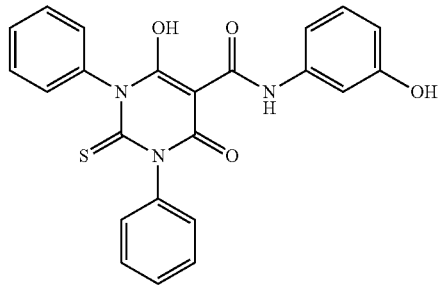 [SMILES: O=C(Nc1cccc(O)c1)c1c(O)n(-c2ccccc2)c(=S)n(-c2ccccc2)c1=O]

Titled compound was synthesized following the general procedure previously described using intermediate 2 (100 mg, 0.27 mmol) and 3-aminophenol (30 mg, 0.27 mmol) obtaining 29.6 mg of pure compound (yield 26%).

Characterization: Rt=1.84 min; MS (ESI) m/z: 432.3 [M-H]⁻. [M-H]⁻ calculated: 432.1. 1 H-NMR (400 MHz, CDCl₃) δ 11.84 (s, 1H), 7.68-7.43 (m, 6H), 7.33 (t, J=6.9 Hz, 4H), 7.24 (t, J=8.1 Hz, 1H), 7.13 (s, 1H), 6.98 (d, J=8.0 Hz, 1H), 6.76-6.68 (m, 1H), 5.08 (s, 1H).

Example 6

Synthesis of 4-hydroxy-6-oxo-1,3-diphenyl-2-thioxo-N-(3,4,5-trimethoxyphenyl)pyrimidine-5-carboxamide (Compound 6, Scheme 1)

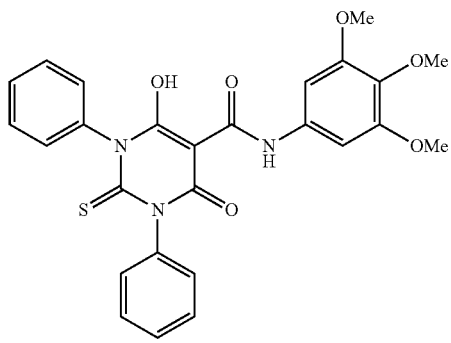 [SMILES: COc1cc(NC(=O)c2c(O)n(-c3ccccc3)c(=S)n(-c3ccccc3)c2=O)cc(OC)c1OC]

Titled compound was synthesized following the general procedure previously described using intermediate 2 (100 mg, 0.27 mmol) and 3,4,5-trimethoxyaniline (50.7 mg, 0.27 mmol) obtaining 118.3 mg of pure compound (yield 86%).

Characterization: Rt=2.04 min; MS (ESI) m/z: 506.1 [M-H]⁺. [M-H]⁺ calculated: 506.1. 1H-NMR (400 MHz, CDCl₃) δ 11.82 (s, 1H), 7.60-7.52 (m, 4H), 7.52-7.46 (m, 2H), 7.36-7.29 (m, 2H), 7.34-7.27 (m, 1H), 6.75 (s, 2H), 3.84 (s, 3H), 3.82 (s, 6H).

Example 7

Synthesis of N-(3,5-dimethoxyphenyl)-4-hydroxy-6-oxo-1,3-diphenyl-2-thioxo-pyrimidine-5-carboxamide (Compound 7, Scheme 1)

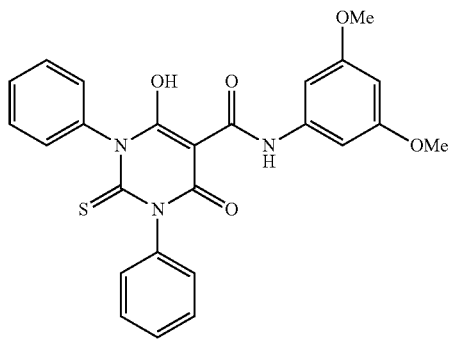 [SMILES: COc1cc(NC(=O)c2c(O)n(-c3ccccc3)c(=S)n(-c3ccccc3)c2=O)cc(OC)c1]

Titled compound was synthesized following the general procedure previously described using intermediate 2 (100 mg, 0.27 mmol) and 3,5-dimethoxyaniline (41 mg, 0.27 mmol) obtaining 83.2 mg of pure compound (yield 65%).

Characterization: Rt=2.13 min; MS (ESI) m/z: 476.3 [M-H]⁺, [M-H]⁺ calculated: 476.1. 1H-NMR (400 MHz, CDCl₃) δ 11.83 (s, 1H), 7.65-7.45 (m, 6H), 7.37-7.28 (m, 4H), 6.68 (d, J=2.0 Hz, 2H), 6.33 (t, J=2.0 Hz, 1H), 3.76 (s, 6H), 1.59 (s, 1H).

Example 8

Synthesis of 4-hydroxy-N-(4-methoxyphenyl)-6-oxo-1,3-diphenyl-2-thioxo-pyrimidine-5-carboxamide (Compound 8, Scheme 1)

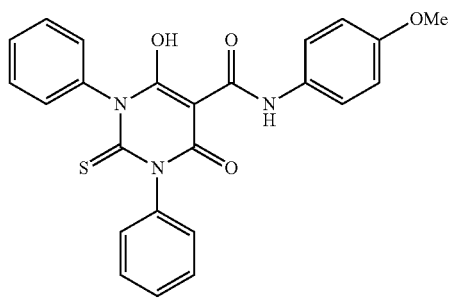 [SMILES: COc1ccc(NC(=O)c2c(O)n(-c3ccccc3)c(=S)n(-c3ccccc3)c2=O)cc1]

Titled compound was synthesized following the general procedure previously described using compound 3 (100 mg, 0.27 mmol) and p-anisidine (34.0 mg, 0.27 mmol) obtaining 60.3 mg of pure compound (yield 22%).

Characterization: Rt=2.10 min; MS (ESI) m/z: 446.1 [M-H]+, [M-H]+ calculated: 446.1169. 1 H-NMR (400 MHz, CDCl$_3$) δ 11.76 (s, 1H), 7.58-7.52 (m, 4H), 7.52-7.46 (m, 3H), 7.41-7.36 (m, 2H), 7.34-7.28 (m, 4H), 6.92-6.88 (d, J=2.1 Hz, 2H), 3.81 (s, 3H).

Example 9

Topo II Activity Tests

The topo II activity of the prepared compounds was experimentally confirmed according to a standard cleavage assay: it requires the use of high enzyme concentration and the block of the enzymatic reaction with a denaturation step. The compounds concentration at which the formation of linear DNA was observed is reported in Table 1. For this activity, all compounds were compared to the leading inhibitor, Merbarone, and to the clinically used drug Etoposide. The tested compounds are in between these two reference compounds. Furthermore, the same compounds were tested for DNA binding properties by UV titrations. It was found that none of the new derivatives show any relevant affinity for the nucleic acid, alone.

The structures of the compounds of Examples 3-10 with their activity data are reported in the following Table.

The substituent group R reported on the left side of the Table represents the moiety

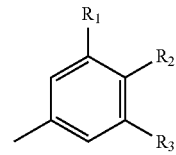

of the compound of formula (I).

TABLE 1

Exemplary compounds with activity data

| R | Topo II inhibition (μM) | Cleavage complex (μM) | DNA binding | HeLa (μM) | MCF7 (μM) | A549 (μM) | DU145 (μM) |
|---|---|---|---|---|---|---|---|
| 3,5-diOMe-4-OH-phenyl | 120.0 ± 15.1 | 200 | NO | 18.1 ± 0.8 | 53.5 ± 1.9 | 17.5 ± 1.1 | 26.7 ± 0.1 |
| 4-OH-phenyl | 150.0 ± 19.0 | 200 | NO | 42.9 ± 6.1 | 66.1 ± 7.5 | 37.1 ± 3.7 | 42.5 ± 7.7 |
| 3-OMe-phenyl | 30.5 ± 5.7 | 100 | NO | 8.5 ± 0.5 | 14.0 ± 0.9 | 6.9 ± 0.2 | 12.5 ± 1.5 |

TABLE 1-continued

| Structure | | | | | | | |
|---|---|---|---|---|---|---|---|
| 3-OH phenyl | 200 ± 22 | NO | NO | 39.1 ± 0.7 | 94.2 ± 3.1 | 59.4 ± 6.1 | 49.6 ± 2.7 |
| 2,3,4-triOMe phenyl | >200 | n.a. | n.a. | n.a. | n.a. | n.a. | n.a. |
| 3,5-diOMe phenyl | >200 | n.a. | n.a. | n.a. | n.a. | n.a. | n.a. |
| 4-OMe phenyl | >200 | n.a. | n.a. | n.a. | n.a. | n.a. | n.a. | n.a.: data non available

The invention claimed is:

1. A method of treating a subject having cancer, said method comprising:
  administering to the subject having cancer, wherein said cancer is selected from breast cancer, cervical cancer, lung cancer and/or prostate cancer, a compound of formula (I)

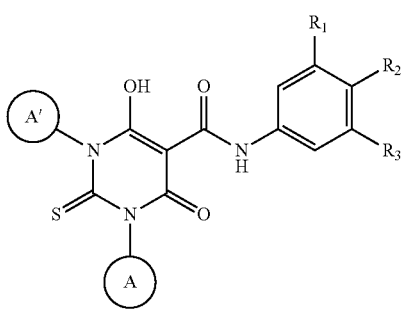

(I)

wherein
  $R_1$, $R_2$, $R_3$ are independently hydrogen, halogen, hydroxyl, alkoxyalkyl containing a total of 1 to 4 carbon atoms, amino, aminoalkyl containing a total of 1 to 4 carbon atoms, aminodialkyl containing a total of 2 to 8 carbon atoms, and wherein at least one of $R_1$, $R_2$, $R_3$ is not H;
  Ⓐ and are independently an optionally substituted heteroaromatic 6-membered ring containing 1 or 2 nitrogen atoms or an optionally substituted 6-membered aryl.

2. The method of claim 1, wherein A and/or A' are an aryl.

3. The method of claim 2, wherein said aryl is substituted with a group $C_1$-$C_6$ alkyl, $C_1$-$C_6$ alkoxyl or hydroxyl.

4. The method of claim 1, wherein A and/or A' are an optionally substituted heteroaromatic 6-membered ring containing 2 nitrogen atom.

5. The method of claim 1, wherein A and/or A' are an optionally substituted heteroaromatic 6-membered ring containing 2 nitrogen atoms.

6. The method claim 1, wherein two of $R_1$, $R_2$, $R_3$ are independently hydroxyl, alkoxyalkyl containing of 1 to 4 carbon atoms.

7. The method of claim 1, wherein at least one of $R_1$, $R_2$, $R_3$ is alkoxyalkyl containing of 1 to 4 carbon atoms.

8. The method claim 1, wherein $R_2$ is H and $R_1$ and $R_3$ independently are OH or an alkoxyalkyl containing of 1 to 4 carbon atoms.

9. The method of claim 8, wherein $R_1$ and $R_3$ are an alkoxyalkyl with 1 to 4 carbon atoms.

10. The method claim 2, further comprising administering a compound of formula (I) in combination with an anti-cancer agent.

11. A process for producing a compound of formula (I) according to claim 1, said process comprising:
  a) adding methyl 3-chloro-3-oxopropionate to a solution of N,N'-Diphenylthiourea in a first organic solvent to give 1,3-Diphenyl-2-thiobarbituric acid which is Intermediate 1,
  b) adding ethylchloroformate to a solution of the Intermediate 1 in 4-dimethylamino-pyridine and pyridine in a second organic solvent to give ethyl 4-hydroxy-6-oxo-1,3-diphenyl-2-thioxo-pyrimidine-5-carboxylate which is Intermediate 2
  c) Reacting Intermediate 2 with aniline of formula R—$NH_2$
wherein R represents

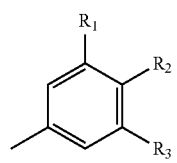

and $R_1$, $R_2$, $R_3$ are independently hydrogen, halogen, hydroxyl, alkoxyalkyl containing a total of 1 to 4 carbon atoms, amino, aminoalkyl containing a total of 1 to 4 carbon atoms, aminodialkyl containing a total of 2 to 8 carbon atoms, and wherein at least one of $R_1$, $R_2$, R₃ is not H, wherein said reacting occurs in presence of a third organic solvent to give the compound of formula (I).

12. The process of claim 11 wherein the aniline R—NH₂ is of formula

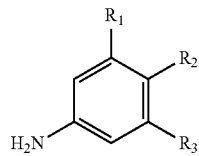

wherein R₁ and R₃ are OCH₃, R₂ is OH and is prepared by
a) adding tert-Butyl nitrite to a solution of 2,6-dimethoxyphenol in an organic solvent to give

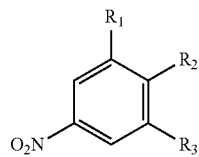

which is Intermediate 3 wherein R1 and R3 are OCH3, R2 is OH;
b) adding 1,4-cyclohexadiene to Intermediate 3 in presence of a catalyzer on activated carbon suspension in ethanol to give

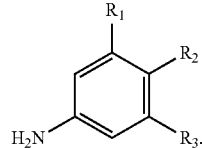

13. The process of claim 11, wherein the first and second organic solvent is dichloromethane and the third organic solvent is dimethylformamide.

14. The process of claim 11, wherein said reacting Intermediate 2 with aniline of formula R—NH2 is carried out under N₂ atmosphere.

15. The method of claim 2, wherein A and/or A' is a phenyl.

16. The method of claim 4, wherein A and/or A' is pyridine.

17. The method of claim 5, wherein A and/or A' are selected from pyridazine, pyrimidine, pyrazine and diazine.

18. The method of claim 7, wherein at least one of R1, R2, R3 is methoxyl.

19. The method of claim 9, wherein R1 and R3 are methoxyl.

20. The method of claim 10, wherein the anti-cancer agent is selected from doxorubicin, daunorubicin, etoposide, cisplatin, oxaliplatin, carboplatin, gemcitabine, 5-fluorouracil, capecitabine, tegafur-uracil (UFT), dacarbazine, fenretinide, camptothecin, irinotecan, fludarabine, vinblastine, taxol, mitomycin C and mixtures thereof.

* * * * *

UNITED STATES PATENT AND TRADEMARK OFFICE
CERTIFICATE OF CORRECTION

PATENT NO. : 11,008,293 B2
APPLICATION NO. : 16/494433
DATED : May 18, 2021
INVENTOR(S) : Marco De Vivo Page 1 of 1

It is certified that error appears in the above-identified patent and that said Letters Patent is hereby corrected as shown below:

In the Claims

Claim 1, Column 19, Line 56, delete "Ⓐ and are independently" and insert --Ⓐ and Ⓐ' are independently-- in its place.

Claim 12, Column 21, Lines 28-29, delete "wherein R1 and R3 are OCH3, R2 is OH" and insert --wherein $R_1$ and $R_3$ are $OCH_3$, $R_2$ is OH-- in its place.

Claim 14, Column 22, Line 13, delete "formula R-NH2" and insert --formula $R-NH_2$-- in its place.

Claim 18, Column 22, Lines 21-22, delete "at least one of R1, R2, R3" and insert --at least one of $R_1$, $R_2$, $R_3$-- in its place.

Claim 19, Column 22, Line 23, delete "wherein R1 and R3 are" and insert --wherein $R_1$ and $R_3$ are-- in its place.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*